United States Patent
Yang et al.

(10) Patent No.: US 7,781,077 B2
(45) Date of Patent: *Aug. 24, 2010

(54) PHOSPHORESCENT LIGHT-EMITTING DEVICE WITH DOPED IRIDIUM-COMPLEX

(75) Inventors: Chun-Hui Yang, Hualian County (TW); Cheng-Hung Lin, Changhua County (TW)

(73) Assignee: Au Optronics Corporation, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/287,470

(22) Filed: Oct. 8, 2008

(65) Prior Publication Data

US 2009/0039779 A1 Feb. 12, 2009

Related U.S. Application Data

(62) Division of application No. 11/117,170, filed on Apr. 27, 2005, now Pat. No. 7,498,437.

(51) Int. Cl.
*H01L 51/54* (2006.01)
*C09K 11/00* (2006.01)

(52) U.S. Cl. ............ 428/690; 428/917; 313/504; 313/506; 257/40; 257/E51.044; 252/301.16; 546/4; 546/6; 548/106

(58) Field of Classification Search ............ 546/6, 546/10
See application file for complete search history.

(56) References Cited

U.S. PATENT DOCUMENTS

| | | | |
|---|---|---|---|
| 6,097,147 A | 8/2000 | Baldo et al. | 313/506 |
| 6,458,475 B1 | 10/2002 | Adachi et al. | 428/690 |
| 6,626,722 B2 | 9/2003 | Takematsu et al. | 445/24 |
| 6,645,645 B1 | 11/2003 | Adachi et al. | 428/690 |
| 6,783,873 B2 | 8/2004 | Tsuboyama et al. | 428/690 |
| 6,830,828 B2 | 12/2004 | Thompson et al. | 428/690 |
| 6,921,915 B2 | 7/2005 | Takiguchi et al. | 257/40 |
| 2002/0134984 A1 | 9/2002 | Igarashi | 257/79 |
| 2003/0080342 A1* | 5/2003 | Igarashi | 257/79 |
| 2003/0175553 A1 | 9/2003 | Thompson et al. | 428/690 |
| 2004/0137268 A1* | 7/2004 | Igarashi et al. | 428/690 |
| 2004/0260047 A1 | 12/2004 | Chen et al. | 528/4 |
| 2005/0287396 A1 | 12/2005 | Nakamura et al. | 428/690 |

FOREIGN PATENT DOCUMENTS

| | | |
|---|---|---|
| EP | 00676461 B1 | 3/1995 |
| JP | 2002-332291 | 11/2002 |
| JP | 2002-359079 | 12/2002 |
| JP | 2004-355898 | 12/2004 |
| JP | 2006-013222 | 1/2006 |
| JP | 2006-093665 | 4/2006 |
| JP | 2006-100537 | 4/2006 |
| JP | 2006-148012 | 6/2006 |
| WO | WO 2005/038944 A1 | 4/2005 |

OTHER PUBLICATIONS

American Chemical Society; J. Jacob et al.; "Ladder-Type Pentaphenylenes and Their Polymers: Efficient Blue-Light Emitters and Electron-Accepting Materials via a Common Intermediate"; Journal of American Chemical Society, vol. 126, pp. 6987-6995; 2004.
American Chemical Society; W. Shen et al.; "Spirobifluorene-Linked Bisanthracene: An Efficient Blue Emitter with Pronounced Thermal Stability"; Chemical Materials, vol. 16, pp. 930-934; 2004.
American Chemical Society; X. Chen et al.; "High-Efficiency Red-Light Emission from Polyfluorenes Grafted with Cyclometalated Iridium Complexes and Charge Transport Moiety"; Journal of American Chemical Society, vol. 125, pp. 636-637; 2003.
American Chemical Society; A. Sandee et al.; "Solution-Processible Conjugated Electrophosphorescent Polymers"; Journal of American Chemical Society, vol. 126, pp. 7041-7048; 2004.
American Institute of Physics; Y. Niu et al.; "Highly Efficient Red Electrophosphorescent Devices Based on an Iridium Complex with Trifluoromethyl-Substituted Pyrimidine Ligand"; Applied Physics Letters, vol. 85, No. 9, pp. 1619-1621; 2004.
American Chemical Society; K. Brunner et al.; "Carbazole Compounds as Host Materials for Triplet Emitters in Organic Light-Emitting Diodes: Tuning the HOMO Level without Influencing the Triplet Energy in Small Molecules"; Journal of American Chemical Society, vol. 126, pp. 6035-6042; 2004.

* cited by examiner

*Primary Examiner*—D. Lawrence Tarazano
*Assistant Examiner*—Michael Wilson
(74) *Attorney, Agent, or Firm*—Ware, Fressola, Van Der Sluys & Adolphson, LLP

(57) ABSTRACT

A phosphorescent OLED uses a phosphorescent dopant in the emissive layer, the dopant includes a metal complex containing a plurality of moieties linking to a transition metal ion. One or more of the moieties contain a ligand with a C—SP$^3$ carbon center. The transition metal ion can be an iridium ion. The C—SP$^3$ carbon is linked to a chalcogen atom in an ion form, a nitrogen-containing heterocylic ring and two functional groups, wherein each of the functional groups is selected from aryl, alkyl and heteroaryl. The tetrahedral structure of this carbon center hinders close packing and intermolecular interactions and, therefore, renders the transport of holes in the light-emitting device more efficient. With such chemical structure and property, the self-quenching characteristics of the dopant in high doping concentration can be effectively reduced.

8 Claims, 4 Drawing Sheets

PHOSPHORESCENT LIGHT-EMITTING DEVICE WITH DOPED IRIDIUM-COMPLEX

PRIORITY AND CROSS-REFERENCE TO RELATED APPLICATION

This patent application is a divisional application of and claims benefits to U.S. patent application Ser. No. 11/117,170, now U.S. Pat. No. 7,498,437 filed Apr. 27, 2005.

FIELD OF THE INVENTION

The present invention relates generally to an organic light emitting device and, more particularly, to a phosphorescent organic opto-electronic structure.

BACKGROUND OF THE INVENTION

Most organic light emitting diodes contain an organic emissive layer that emits light by fluorescent or phosphorescent luminescence. An organic LED generally comprises an anode, a hole source, an emissive layer (EML), an electron source and a cathode. The hole source may comprise a hole injection layer (HIL) and a hole transport layer (HTL). The electron source generally comprises an electron transport layer (ETL) and possibly an electron injection layer (EIL), as shown in FIG. 1. Some OLEDs also comprise a thin layer of LiF between the electron source and the cathode.

The EML, comprised of a host material doped with one or more luminescent dyes, provides the function of light emission produced by excitons. The excitons are formed as a result of recombination of holes and electrons in the layer.

The excitons in a fluorescent emissive layer are in a singlet excited state and, therefore, only a small percentage of excitons result in fluorescent luminescence. Excitons in a phosphorescent medium are in an excited triplet state and, theoretically, all excitons can result in phosphorescent luminescence.

Adachi et al. (U.S. Pat. No. 6,645,645) discloses a phosphorescent OLED, wherein the emissive layer is made of phenanthroline (BCP) as host material doped with fac-tris(2-phenylpyridine) iridium (Ir(ppy)$_3$).

Baldo et al. U.S. Pat. No. 6,097,147) discloses another OLED wherein the host material for the emission layer is carbazole biphenyl (CBP) doped with 2,3,7,8,12,13,17,18-octaethyl-21H,23H-porphine platinum (II) (PtOEP).

In a phosphorescent OLED, holes from the hole transport layer recombine in the emissive layer with electrons from the electron transport layer to form triplet-based excitons. The triplet-based excitons diffuse over a relatively long distance in the emissive layer before emitting light. It is possible that some of the excitons diffuse to the cathode and are quenched by the cathode, resulting in non-radiative exciton decay. In order to reduce the quenching by the cathode, a hole blocking layer is disposed between the cathode and the emissive layer. The blocking layer can be made of N,N'-diphenyl-N,N'-bis-alpha-anpthylbenzidine (NPD), CBP, aluminum tris (8-hydroxyquioline) (Alq$_3$) and bathocuproine (BCP), for example.

Adachi et al. ("High-efficiency red electrophosphorescence device", Appl. Phys. Lett., Vol. 78, No. 11, 12 March 2001, pp. 1622-1624) discloses a phosphorescent OLED wherein the emissive layer consists of a conductive CBP host doped with a red phosphor bis(2-(2'-benzo[4,5-a]thienyl)pyridinato-N,C$^3$') iridium(acetylacetonate) (Btp$_2$Ir(acac)) and the blocking layer is made from 2,9-dimethyl-4,7-diphenyl-phenanthroline.

Kwong et al. (High operational stability of electrophosphorescent devices", Appl. Phys. Lett., Vol. 81, No. 1, 1 July 2002, pp. 162-164) discloses a phosphorescent OLED wherein the emissive layer is made of CBP doped with Ir(ppy)$_3$ and the blocking layer is made from 2,2',2''-(1,3,5-benzenetriyl) tris-[1-phenyl-1-H-benzimidazole (TPBI), aluminum (III)bis(2- methyl-8-quinolinato) triphenylsilanolate (SAlq), aluminum (III)bis(2-methyl-8-quinolinato )4-phenolate (PAlq) or aluminum (III)bis(2-methyl-8-quinolinato)4-phenylphenolate (BAlq).

In prior art, metal complexes are also used in a blocking layer. For example Thompson et al. (U.S. Patent Application 2003/0175553 A1) discloses that fac-tris(1-phenylpyrazolato-N,C$^2$)iridium(III) (Ir(ppz)$_3$) is used as an electron/exciton blocking material. Thompson et al. also uses metal complexes such as platinum (II)(2-(4',6'-difluorophenyl) pyridinato-N,C$^2$)(2,4-pentanedionato) (FPt, FPl(acac)); platinum (II) (2-(4',6'-difluropheny)pyridinato-N,C$^2$)(2,2,6,6,-tetramethyl-3,5-heptanedionato) (FPt2); platinum (II)(2-(4',6'-difluorophenyl) pyridinato-N,C$^2$)(6-methyl-2,4-heptanedionato) (FPt3); platinum (II)(2-(4',6'-difluorophenyl) pyridinato-N,C$^2$)(3-ethyl-2,4-pentanedionato) (FPt4); iridium-bis(4,6,-F$_2$-phenyl-pyridinato-N,C$^2$)-picolinate (FIr (pic)) and N,N'-meta-dicarbazoloylbenzene (mCP) as dopants in the emissive layer. Igarashi (U.S. Patent Application 2001/0134984 A1) discloses a light-emitting device wherein at least one of the organic layers comprises a transition metal complex containing a moiety which has a transition metal ion linked to two nitrogen ions in a nitrogen-containing structure. The same transition metal ion is linked to at least one nitrogen ion in another moiety. Shen et al. ("Spirobifluorene-Linked Bisanthracene: An Efficient Blue Emitter with Pronounced Thermal Stability", Chem. Mater. 2004, 16, 930-934) discloses the use of spiro-FPA as a blue emitter in an OLED. Jacob et al. ("Ladder-Type Pentaphenylenes and Their Polymers: Efficient Blue-Light Emitters and Electron-Accepting Materials via a Common Intermediate", J. AM. CHEM. SOC. 2004, 126, 6987-6995) discloses a plurality of ladder-type pentaphenylenes for use both hole accepting p-type materials and electron accepting n-type materials in blue OLEDs.

It has been found that when metal complexes are used as dopants with high doping concentration, most of the metal complexes appear to be self-quenching, thereby reducing the emission efficiency in the light-emitting device.

SUMMARY OF THE INVENTION

It is an object of the present invention to reduce the quenching effect and to increase the emission efficiency in a phosphorescent light-emitting device. The present invention uses a variety of metal complexes for use as dopants in the emissive layer and to improve carrier capability of phosphorescent dopants. In particular, each of the metal complexes comprises at least a moiety containing a C-SP$^3$ ligand, the moiety having the structure:

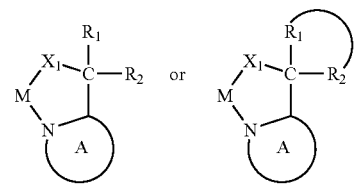

wherein $R_1$ and $R_2$ are functional groups with or without a bond between $R_1$ and $R_2$, $X_1$ represents a chalcogen atom and M represents a transition metal ion. The A ring is a nitrogen-containing heterocylic ring. In particular, $R_1$ and $R_2$ are each individually selected from the group consisting of aryl, alkyl and heteroaryl

DETAILED DESCRIPTION OF THE INVENTION

Figure 2:
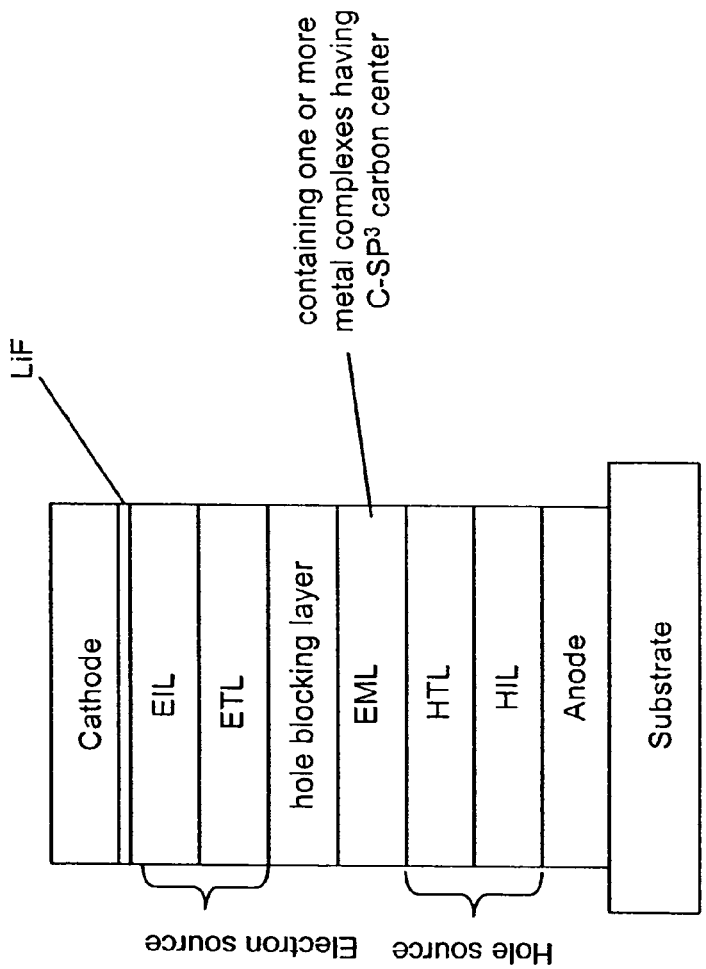
FIG. 2 is a schematic representation of a phosphorescent OLED, according to the present invention.
Figure 1:
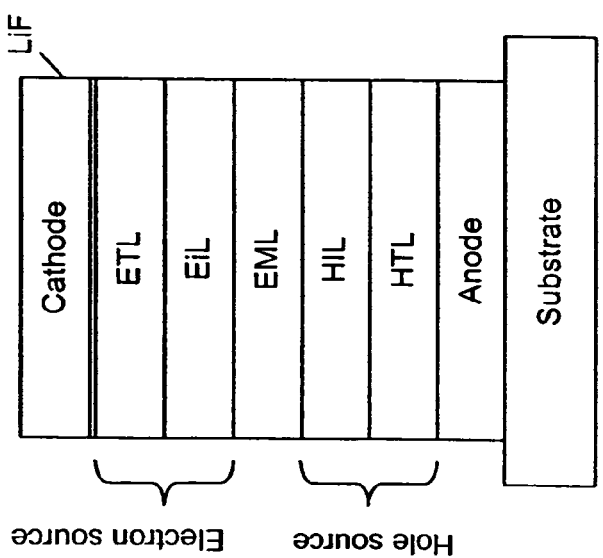
FIG. 1 is a schematic representation showing a typical OLED.

In the phosphorescent dopants as disclosed in prior art, one of the moieties usually contain a ligand composed of an $SP^2$ carbon structure. Metal complexes such as Ir(ppy)$_3$, IrPQ(acac) and FIr(pic) contain such a ligand. $SP^2$ carbon has a major advantage in that the length of conjugated bonds, or the length of the spin-orbital coupling in the ligand can be adjusted in order to change the emission wavelength of the phosphorescent material. For example, the conjugated bonds in the ligand of Ir(ppy)$_3$ and IrPQ(acac) are relatively long and, therefore, Ir(ppy)3 and IrPQ(acac) can be used for phosphorescence in the 520-532 nm range. The conjugated bonds in the ligand in FIr(pic) are shorter and the corresponding phosphorescent wavelength is 470 nm.

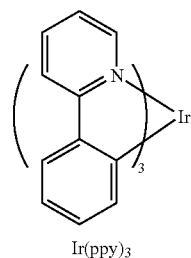

Ir(ppy)$_3$

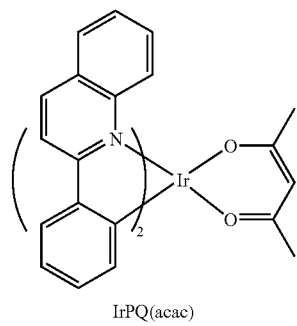

IrPQ(acac)

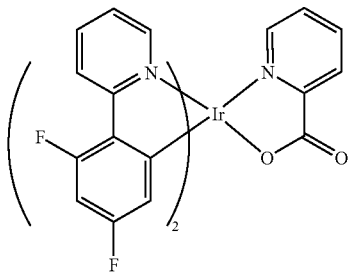

FIr(pic)

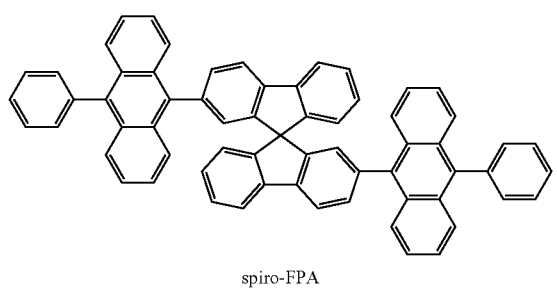

spiro-FPA

The phosphorescent materials, according to the present invention, contain a ligand with an $SP^3$ carbon center. As such, four separate functional groups can be attached to the $SP^3$ carbon. Through the functional groups, the ligand is bonded with a transitional metal ion to form a metal complex. Because the electronic affinity to the $SP^3$ carbon center is different for different functional groups and the functional group may have different physical characteristics due to its location in the ligand, it is possible to adjust the emission wavelength of metal complex by selecting different functional groups.

A ligand with a $SP^3$ carbon center has a tetrahedral structure. A metal complex with such a ligand may have a geometrical shape that reduces the self-quenching characteristics of dopants in high doping concentration.

It should be noted that spiro-FPA has been used as a blue emitter in prior art fluorescent devices (see Shen et al.). Spiro-FPA has two identical anthracene luminophores linked orthogonally around a spirobifluorene core. The tetrahedral nature of $SP^3$ carbon at the spiro center reduces the conjugate bonds in spiro-FPA. As such, spiro-FPA has a fluorescent wavelength of 450 nm. With a high glass transition temperature ($T_g$), an amorphous thin film made of spiro-FPA used in a fluorescent OLED is less vulnerable to heat and, therefore, the device performance is more stable. With the presence of lower-energy flurosphores, Spiro-FPA can serve as efficient energy-transfer donors in a light-emitting device.

The present invention uses a variety of metal complexes for use as dopants in the emissive layer and to improve carrier capability of phosphorescent dopants. In particular, the metal complex comprises at least a moiety containing a C-$SP^3$ ligand, wherein the moiety together with the linked transition metal ion has the structure:

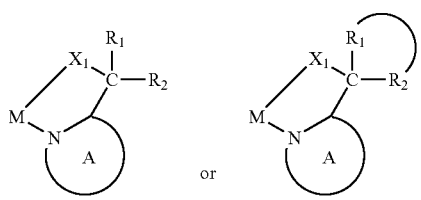

wherein $R_1$ and $R_2$ represent functional groups with or without a bond therebetween. M represents a transition metal ion, $X_1$ represents a chalcogen atom. In particular, $R_1$ and $R_2$ are each individually selected from the group consisting of aryl, alkyl and heteroaryl. The A ring is a nitrogen-containing heterocylic ring, such as wherein
$R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, and $R_{23}$ each represent a functional group. In particular, they are each independently selected from the group consisting of F, CF3, CH3, aryl and alkyl.

The following examples are a few examples of the metal complexes for use as dopants in the emissive layer in a phosphorescent light-emitting device, according to the present invention. These dopants are suitable for use to provide luminescence in the range of 452-550 nm. For example, the compound labeled I in the following examples is suitable for use in a blue OLED.

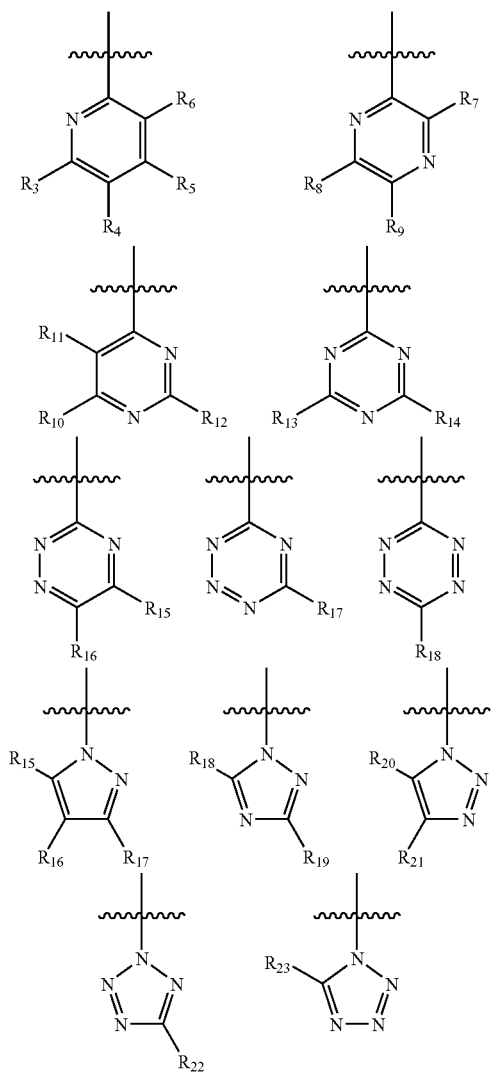

-continued

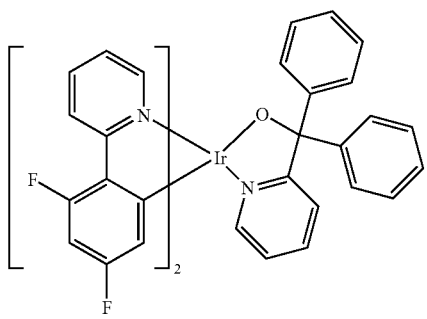

520 nm

E

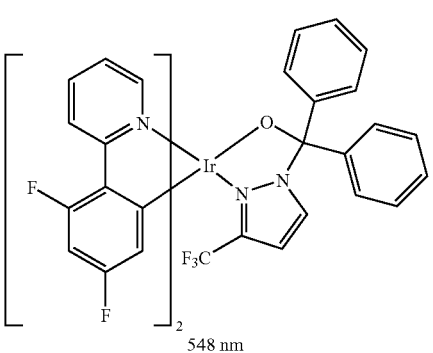

548 nm

F

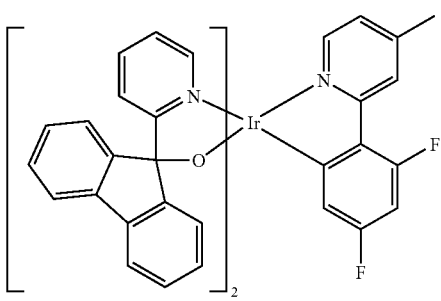

G

-continued

476~489 nm

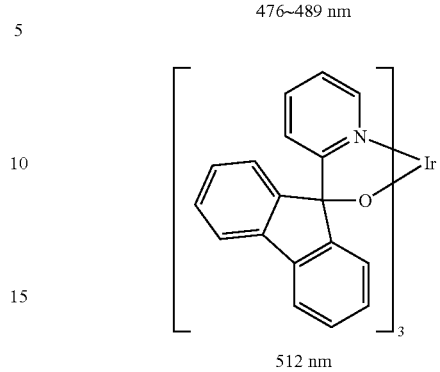

512 nm

H

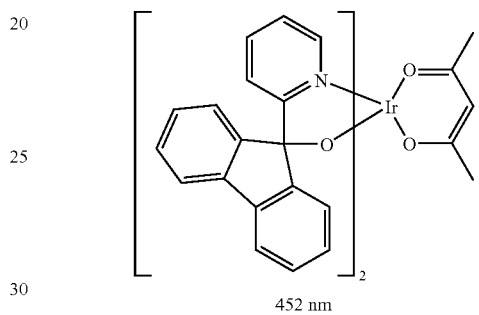

452 nm

I

Synthesis of Exemplary Compounds

Although synthesis of the metal complexes for use in the OLED, according to the present invention, is not part of the claimed invention, it would be useful to show the synthesizing processes. However, these processes are disclosed without the intension of restricting the scope of the present invention defined in the claims.

Synthesis of Compound B

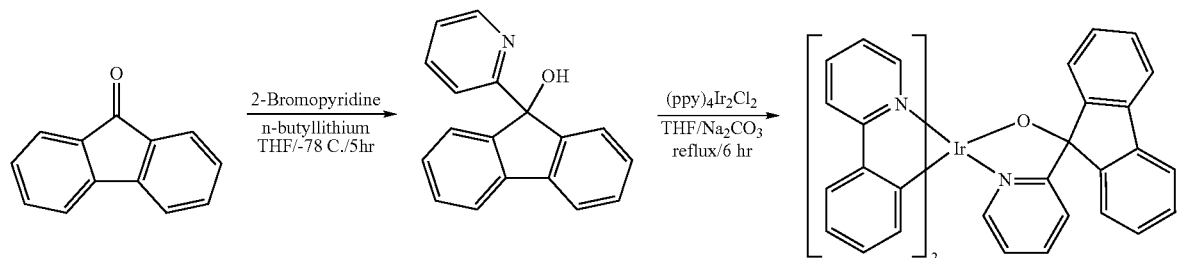

Synthesis of Compound G

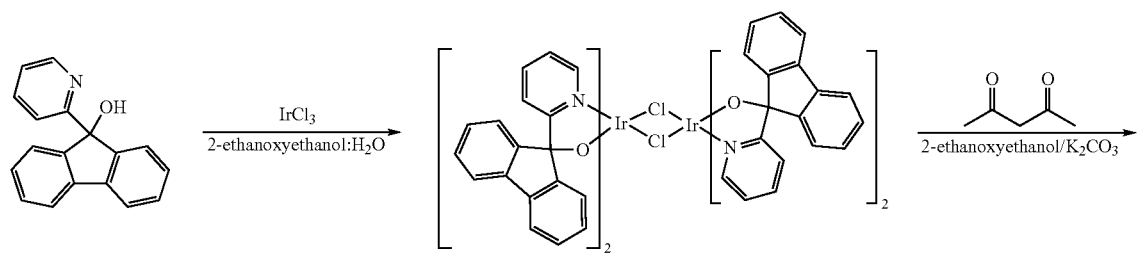

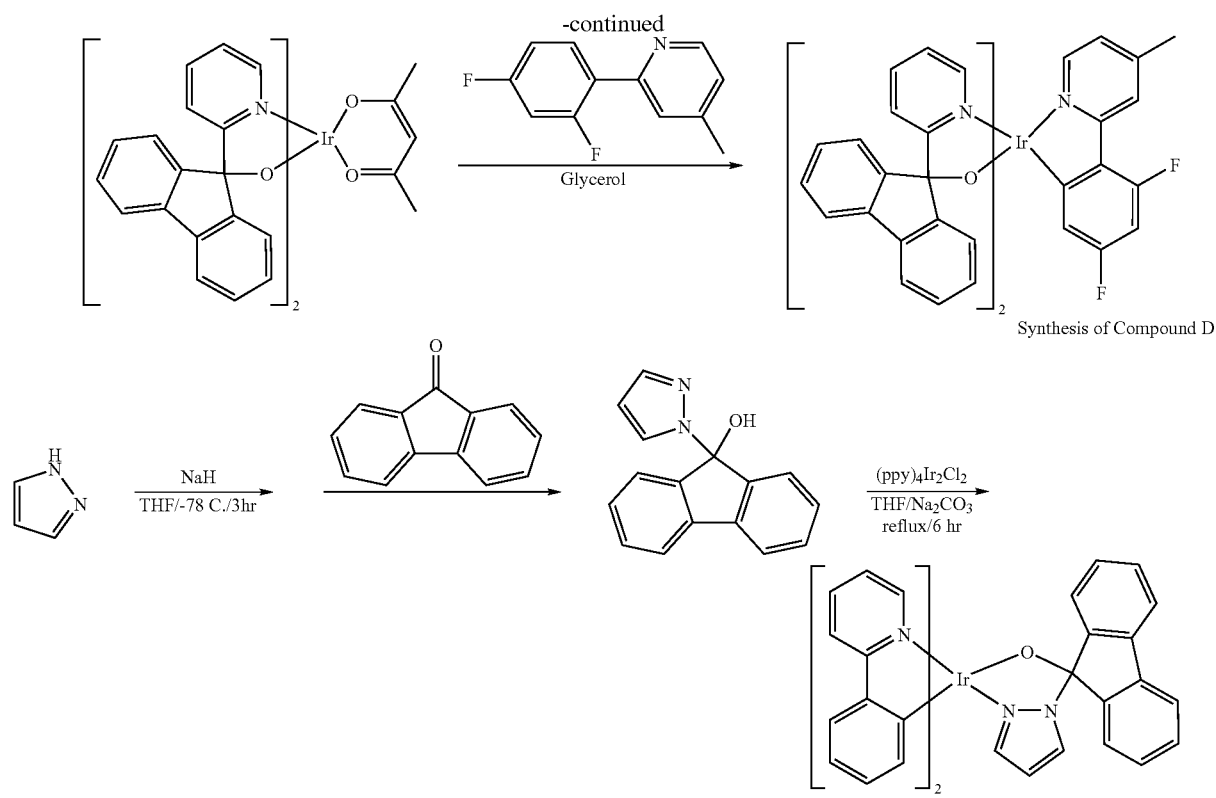

Synthesis of Compound D

Device Example

Cathode: Indium tin oxide (ITO)

Hole source:

Hole injection layer (HIL): copper phthalocyanine (CuPC) or poly(3,4-ethylenedioxythiophene)/poly(styrene sulfonate) (PEDOT:PSS)

Hole transport layer (HTL): N,N'-di(naphthalene-1-yl)-N,N'-diphthalbenzidine (NPB)

Emissive layer: carbazole biphenyl (CBP) doped with Compound E, with dopant concentration of 3%, 5%, 7% and 10%

Hole blocking layer: aluminum (III)bis(2- methyl-8-quinolinato )4-phenylphenolate (BAlq)

Electron source:

Electron transport layer: aluminum tris (8-hydroxyquioline) ($Alq_3$)

Anode: Al

The schematic representation of a phosphorescent organic light-emitting device of the present invention is shown in FIG. 2.

Device Performance

Figure 3:
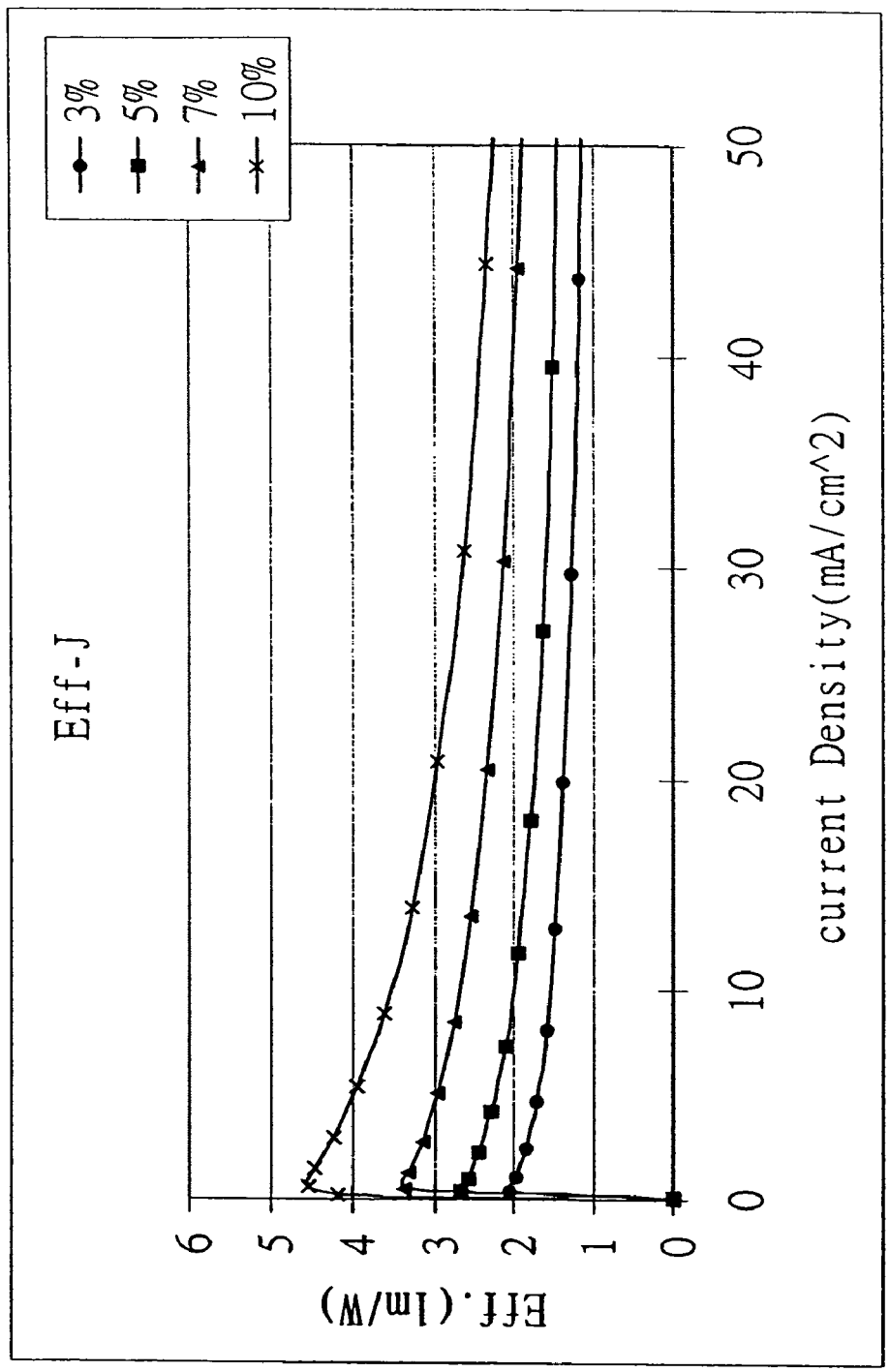
FIG. 3 is a plot of efficiency vs. currently density of an experimental device, according to the present invention.
Figure 4:
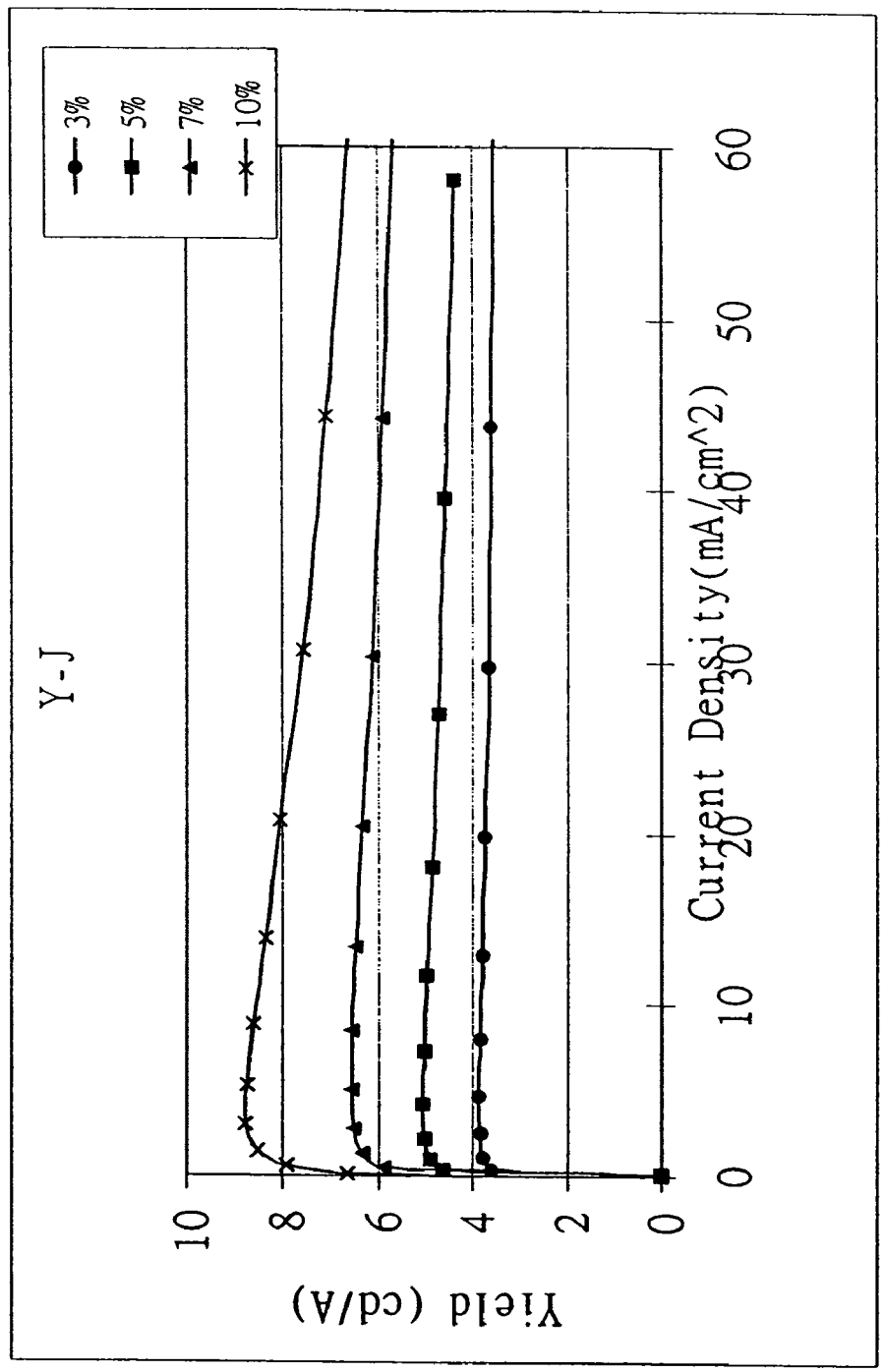
FIG. 4 is a plot of yield vs. current density.
Figure 5:
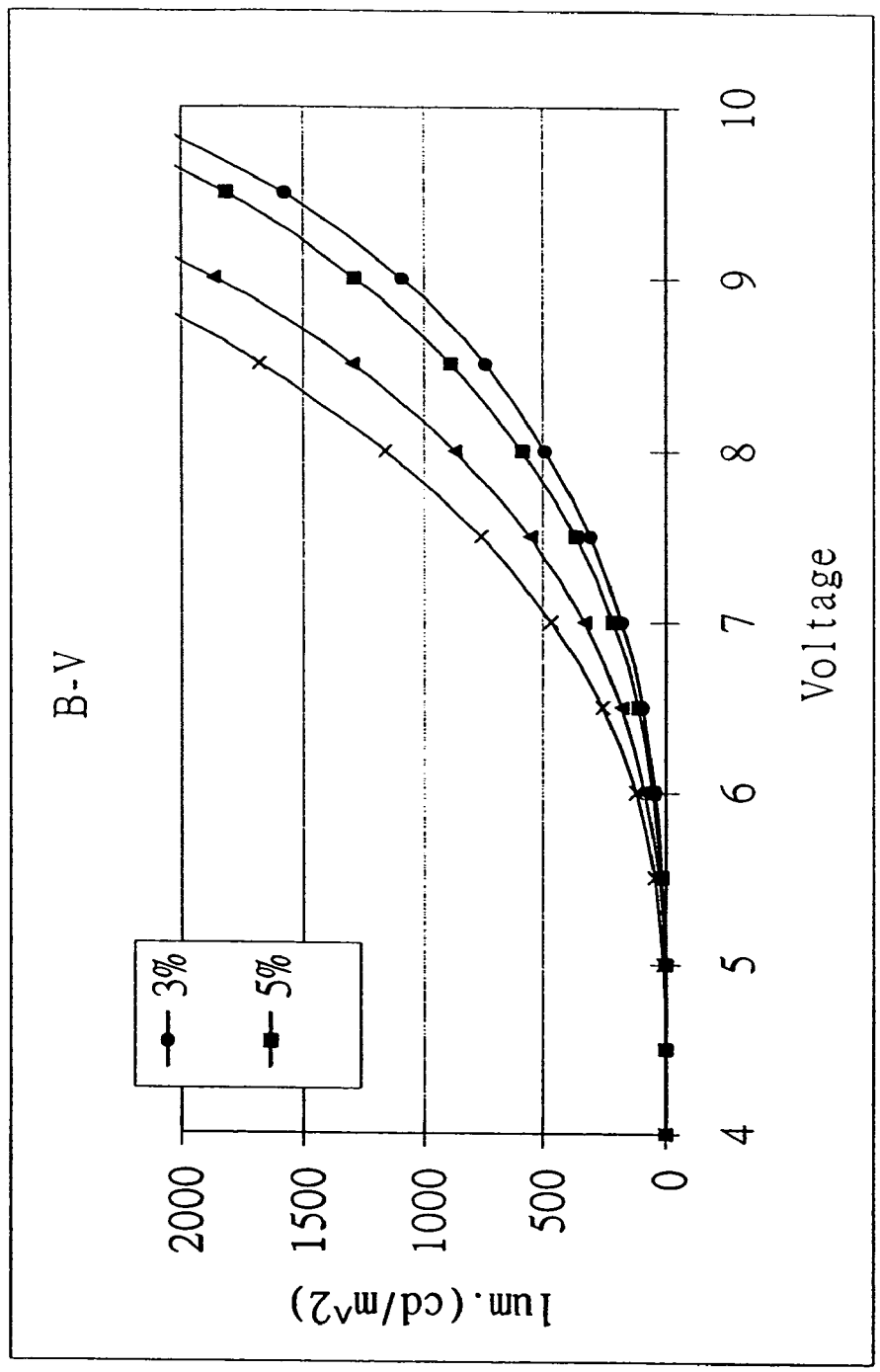
FIG. 5 is a plot of brightness vs. applied voltage.

The efficiency, yield and brightness of the above-described exemplary device are separately shown in FIGS. 3-5. As shown in FIGS. 3-5, at dopant concentration of 10%, the efficiency of the device can reach 4.5 (lm/W), the yield can reach 8.8 (cd/A), and, at applied voltage=7.7 v, the brightness can reach 100 (cd/$m^2$). CIE chromaticity is (0.32, 0.56). It has been found that the efficiency and yield do not improve significantly beyond the dopant concentration of 10%. Furthermore, the efficiency and yield decrease at a much higher concentration.

In sum, the present invention uses a phosphorescent dopant comprising a metal complex, wherein the metal complex containing a plurality of moieties linking to a transition metal ion and one or more of the moieties contain a ligand with a C-$SP^3$ carbon center. The tetrahedral structure of this carbon center hinders close packing and intermolecular interactions and, therefore, renders the transport of holes in the light-emitting device more efficient. With such chemical structure and property, the self-quenching characteristics of the dopant in high doping concentration can be effectively reduced.

Although the invention has been described with respect to one or more embodiments thereof, it will be understood by those skilled in the art that the foregoing and various other changes, omissions and deviations in the form and detail thereof may be made without departing from the scope of this invention.

What is claimed is:

1. A phosphorescent organic light-emitting device comprising:

an anode;

a cathode;

a layer structure disposed between the anode and the cathode, the layer structure comprising:

a hole source adjacent to the anode;

an electron source adjacent to the cathode; and a light-emitting layer disposed between the hole source and the electron source, wherein the light-emitting layer is made of at least a host material doped with at least a dopant made of a metal complex, the metal complex having one of the following four structures:

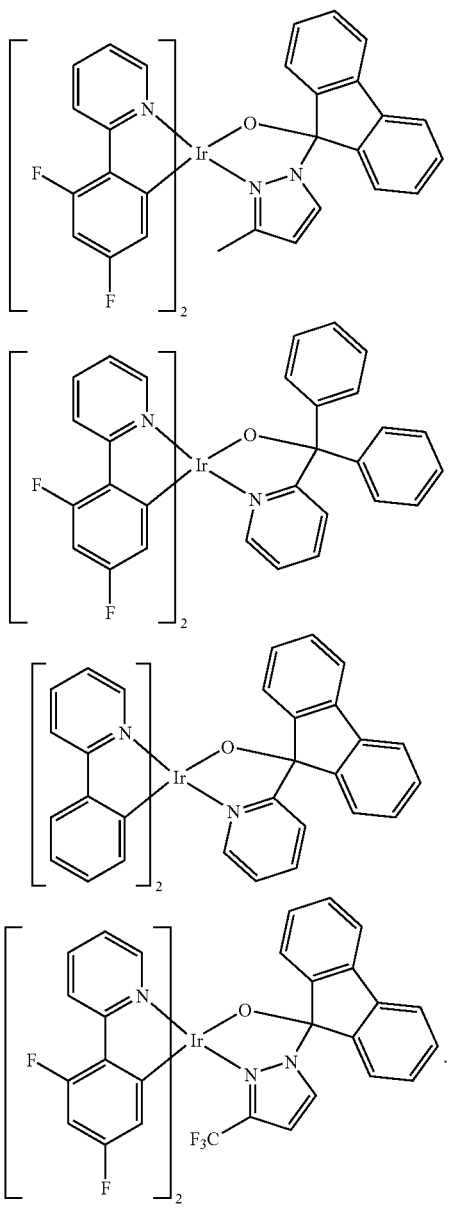

2. The light-emitting device of claim 1, further comprising a layer made substantially of LiF disposed between the electronic source and the cathode.

3. The light-emitting device of claim 1, wherein the hole source comprises a hole injection layer disposed adjacent to the anode and a hole transport layer disposed between the hole injection layer and the light-emitting layer.

4. The light-emitting device of claim 1, wherein the electron source comprises an electron injection layer disposed adjacent to the cathode and an electron transport layer disposed between the electron injection layer and the light-emitting layer.

5. A phosphorescent organic light-emitting device comprising:
an anode;
a cathode;
a layer structure disposed between the anode and the cathode, the layer structure comprising:
a hole source adjacent to the anode;
an electron source adjacent to the cathode; and
a light-emitting layer disposed between the hole source and the electron source, wherein the light-emitting layer is made of at least a host material doped with at least a dopant made of a metal complex, wherein the metal complex having one of the following two structures:

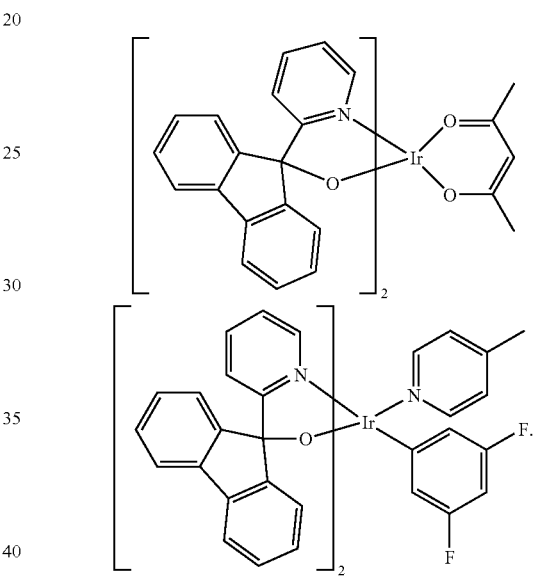

6. The light-emitting device of claim 5, further comprising a layer made substantially of LiF disposed between the electron source and the cathode.

7. The light-emitting device of claim 5, wherein the hole source comprises a hole injection layer disposed adjacent to the anode and a hole transport layer disposed between the hole injection layer and the light-emitting layer.

8. The light-emitting device of claim 5, wherein the electron source comprises an electron injection layer disposed adjacent to the cathode and an electron transport layer disposed between the electron injection layer and the light-emitting layer.

* * * * *